(12) United States Patent
Wollenberg et al.

(10) Patent No.: US 7,648,837 B2
(45) Date of Patent: Jan. 19, 2010

(54) HIGH THROUGHPUT SCREENING METHODS FOR LUBRICATING OIL COMPOSITIONS

(75) Inventors: Robert H. Wollenberg, Orinda, CA (US); Thomas J. Balk, San Francisco, CA (US)

(73) Assignee: Chevron Oronite Company, LLC, San Ramon, CA (US)

( * ) Notice: Subject to any disclaimer, the term of this patent is extended or adjusted under 35 U.S.C. 154(b) by 0 days.

(21) Appl. No.: 12/082,217

(22) Filed: Apr. 9, 2008

(65) Prior Publication Data
US 2009/0029474 A1  Jan. 29, 2009

Related U.S. Application Data

(63) Continuation of application No. 10/699,508, filed on Oct. 31, 2003, now abandoned.

(51) Int. Cl.
*G01N 33/26* (2006.01)
(52) U.S. Cl. .............. 436/60; 436/41; 436/55; 436/164; 422/67; 422/68.1; 422/82.05; 508/110; 506/7; 506/33; 506/37; 506/39; 506/40; 702/30
(58) Field of Classification Search ............. 436/43, 436/55, 60, 164, 165; 422/61, 67, 68.1, 82.05, 422/82.09; 508/110; 506/7, 24, 33, 34, 37, 506/39, 40; 702/30
See application file for complete search history.

(56) References Cited

U.S. PATENT DOCUMENTS

| 5,236,610 A | 8/1993 | Perez et al. |
|---|---|---|
| 5,337,599 A | 8/1994 | Hundere et al. |
| 5,959,297 A | 9/1999 | Weinberg et al. |
| 5,985,356 A | 11/1999 | Shultz et al. |
| 5,993,662 A | 11/1999 | Garr et al. |
| 6,004,617 A | 12/1999 | Shultz et al. |
| 6,030,917 A | 2/2000 | Weinberg et al. |
| 6,034,775 A | 3/2000 | McFarland et al. |
| 6,045,671 A | 4/2000 | Wu et al. |
| 6,087,181 A | 7/2000 | Cong |
| 6,149,882 A | 11/2000 | Guan et al. |
| 6,157,449 A | 12/2000 | Hajduk |
| 6,175,409 B1 | 1/2001 | Nielsen et al. |

(Continued)

FOREIGN PATENT DOCUMENTS

EP    1233361    8/2002

(Continued)

OTHER PUBLICATIONS

Derwent Abstract Accession No. 2001-209710/21, RU 2161306-C2 (Novolipetsk Metallurgy Combine Stock Co) Dec. 27, 2000 abstract.

*Primary Examiner*—Maureen M Wallenhorst
(74) *Attorney, Agent, or Firm*—Claude J. Caroli, Esq.; M. Carmen & Associates, PLLC

(57) ABSTRACT

A method for determining oxidation stability for a plurality of different lubricating oil composition samples is provided. The methods can advantageously be optimized using combinatorial chemistry, in which a database of combinations of lubricating oil compositions is generated. As market conditions vary and/or product requirements or customer specifications change, conditions suitable for forming desired products can be identified with little or no downtime.

19 Claims, 3 Drawing Sheets

U.S. PATENT DOCUMENTS

| | | |
|---|---|---|
| 6,182,499 B1 | 2/2001 | McFarland et al. |
| 6,187,164 B1 | 2/2001 | Warren et al. |
| 6,248,540 B1 | 6/2001 | Weinberg et al. |
| 6,260,407 B1 | 7/2001 | Petro et al. |
| 6,265,226 B1 | 7/2001 | Petro et al. |
| 6,296,771 B1 | 10/2001 | Miroslav |
| 6,326,090 B1 | 12/2001 | Schultz et al. |
| 6,336,353 B2 | 1/2002 | Matsiev et al. |
| 6,345,528 B2 | 2/2002 | Petro et al. |
| 6,346,290 B1 | 2/2002 | Schultz et al. |
| 6,371,640 B1 | 4/2002 | Hajduk et al. |
| 6,373,570 B1 | 4/2002 | McFarland et al. |
| 6,393,895 B1 | 5/2002 | Matsiev et al. |
| 6,393,898 B1 | 5/2002 | Hajduk et al. |
| 6,395,552 B1 | 5/2002 | Borade et al. |
| 6,401,519 B1 | 6/2002 | McFarland et al. |
| 6,406,632 B1 | 6/2002 | Safir et al. |
| 6,410,331 B1 | 6/2002 | Schultz et al. |
| 6,419,881 B1 | 7/2002 | Weinberg et al. |
| 6,420,179 B1 | 7/2002 | Schultz et al. |
| 6,436,292 B1 | 8/2002 | Petro |
| 6,438,497 B1 | 8/2002 | Mansky et al. |
| 6,440,745 B1 | 8/2002 | Weinberg et al. |
| 6,441,901 B2 | 8/2002 | McFarland et al. |
| 6,461,515 B1 | 10/2002 | Safir et al. |
| 6,468,806 B1 | 10/2002 | McFarland et al. |
| 6,475,391 B2 | 11/2002 | Safir et al. |
| 6,484,567 B1 | 11/2002 | Hajduk et al. |
| 6,491,816 B2 | 12/2002 | Petro |
| 6,508,984 B1 | 1/2003 | Turner et al. |
| 6,519,032 B1 | 2/2003 | Kuebler et al. |
| 6,528,026 B2 | 3/2003 | Hajduk et al. |
| 6,535,284 B1 | 3/2003 | Hajduk et al. |
| 6,535,824 B1 | 3/2003 | Mansky et al. |
| 6,536,944 B1 | 3/2003 | Archibald et al. |
| 6,541,271 B1 | 4/2003 | McFarland et al. |
| 6,553,318 B2 | 4/2003 | Mansky |
| 6,576,906 B1 | 6/2003 | Archibald et al. |
| 6,577,392 B1 | 6/2003 | Nielsen et al. |
| 6,582,116 B2 | 6/2003 | Nielsen |
| 6,605,473 B1 | 8/2003 | Hajduk et al. |
| 6,644,101 B2 | 11/2003 | Hajduk et al. |
| 6,649,413 B1 | 11/2003 | Schultz et al. |
| 6,650,102 B2 | 11/2003 | Hajduk et al. |
| 6,653,138 B1 | 11/2003 | Turner et al. |
| 6,655,194 B2 | 12/2003 | Hajduk et al. |
| 6,658,429 B2 | 12/2003 | Dorsett, Jr. |
| 6,664,067 B1 | 12/2003 | Hajduk et al. |
| 6,668,622 B2 | 12/2003 | Hajduk et al. |
| 6,670,298 B1 | 12/2003 | Weinberg et al. |
| 6,679,130 B2 | 1/2004 | Hajduk et al. |
| 6,681,618 B2 | 1/2004 | Hajduk et al. |
| 6,686,205 B1 | 2/2004 | Shultz et al. |
| 6,690,179 B2 | 2/2004 | Hajduk et al. |
| 7,462,490 B2 * | 12/2008 | Wollenberg et al. ........... 436/60 |
| 2002/0023507 A1 | 2/2002 | Hajduk et al. |
| 2002/0028456 A1 | 3/2002 | Mansky et al. |
| 2002/0029621 A1 | 3/2002 | Hajduk et al. |
| 2002/0032531 A1 | 3/2002 | Mansky et al. |
| 2002/0090320 A1 | 7/2002 | Burow et al. |
| 2002/0098332 A1 | 7/2002 | Warren et al. |
| 2002/0148282 A1 | 10/2002 | Hajduk et al. |
| 2002/0155036 A1 | 10/2002 | Hajduk et al. |
| 2002/0164275 A1 | 11/2002 | Wheeler et al. |
| 2003/0007152 A1 | 1/2003 | McFarland et al. |
| 2003/0032198 A1 | 2/2003 | Lugmair et al. |
| 2003/0032205 A1 | 2/2003 | McFarland et al. |
| 2003/0037601 A1 | 2/2003 | Mansky et al. |
| 2003/0037620 A1 | 2/2003 | Mansky |
| 2003/0041653 A1 | 3/2003 | Matsiev et al. |
| 2003/0041671 A1 | 3/2003 | Hajduk et al. |
| 2003/0041672 A1 | 3/2003 | Hajduk et al. |
| 2003/0041676 A1 | 3/2003 | Hajduk et al. |
| 2003/0054740 A1 | 3/2003 | Mansky |
| 2003/0055587 A1 | 3/2003 | Wang et al. |
| 2003/0056576 A1 | 3/2003 | Mansky |
| 2003/0068829 A1 | 4/2003 | Giaquinta et al. |
| 2003/0097871 A1 | 5/2003 | Mansky |
| 2003/0100119 A1 | 5/2003 | Weinberg et al. |
| 2003/0100453 A1 | 5/2003 | O'Rear |
| 2003/0127776 A1 | 7/2003 | Carlson et al. |
| 2003/0133113 A1 | 7/2003 | Hajduk et al. |
| 2003/0138025 A1 | 7/2003 | Archibald et al. |
| 2003/0141613 A1 | 7/2003 | Hajduk et al. |
| 2003/0142309 A1 | 7/2003 | Kuebler et al. |
| 2003/0157721 A1 | 8/2003 | Turner et al. |
| 2003/0161763 A1 | 8/2003 | Erden et al. |
| 2003/0169638 A1 | 9/2003 | Nielsen |
| 2003/0171226 A1 | 9/2003 | Gatto |
| 2003/0190260 A1 | 10/2003 | Wheeler et al. |
| 2003/0203500 A1 | 10/2003 | Carlson et al. |
| 2003/0211016 A1 | 11/2003 | Dales et al. |
| 2003/0218467 A1 | 11/2003 | Carlson et al. |
| 2003/0219906 A1 | 11/2003 | Giaquinta et al. |
| 2004/0123650 A1 | 7/2004 | Kolosov et al. |

FOREIGN PATENT DOCUMENTS

| | | |
|---|---|---|
| WO | WO 95/13538 | 5/1995 |
| WO | WO 02/07870 | 1/2002 |

* cited by examiner

HIGH THROUGHPUT SCREENING METHODS FOR LUBRICATING OIL COMPOSITIONS

PRIORITY

This application is a continuation of U.S. patent application Ser. No. 10/699,508, filed Oct. 31, 2003, now abandoned, the contents of which are incorporated herein by reference.

BACKGROUND OF THE INVENTION

1. Technical Field

The present invention relates generally to methods for high throughput screening of lubricating oil compositions.

2. Description of the Related Art

The use of a combinatorial approach for materials synthesis is a relatively new area of research aimed at using rapid synthesis and screening methods to build libraries of polymeric, inorganic or solid state materials. For example, advances in reactor technology have empowered chemists and engineers to rapidly produce large libraries of discrete organic molecules in the pursuit of new drug discovery, which have led to the development of a growing branch of research called combinatorial chemistry. Combinatorial chemistry generally refers to methods and materials for creating collections of diverse materials or compounds—commonly known as libraries—and to techniques and instruments for evaluating or screening libraries for desirable properties.

Presently, research in the lubricant industry involves individually forming candidate lubricating oil compositions and then performing a macro-scale analysis of the candidate compositions by employing a large amount of the candidate to be tested. Additionally, the methods employed for testing each candidate composition require manual operation. This, in turn, significantly reduces the number of compositions that can be tested and identified as leading lubricating oil compositions.

Drawbacks associated with conventional screening procedures can be seen as follows. For example, governmental and automotive industry pressure towards reducing the phosphorous and sulfur content of lubricating oil compositions used as, for example, passenger car and heavy duty diesel engine oils, is leading to new research to identify oil compositions which can satisfy certain tests such as, for example, oxidation, wear and compatibility tests, while containing low levels of phosphorous and sulfur. In this context, United States Military Standards MIL-L-46152E and the ILSAC Standards defined by the Japanese and United States Automobile Industry Association at present require the phosphorous content of engine oils to be at or below 0.10 wt. % with future phosphorous content being proposed to even lower levels, e.g., 0.08 wt. % by January, 2004 and below 0.05 wt. % by January, 2006. Also, at present, there is no industry standard requirement for sulfur content in engine oils, but it has been proposed that the sulfur content be below 0.2 wt. % by January, 2006. Thus, it would be desirable to decrease the amount of phosphorous and sulfur in lubricating oils still further, thereby meeting future industry standard proposed phosphorous and sulfur contents in the engine oil while still retaining the oxidation or corrosion inhibiting properties and antiwear properties of the higher phosphorous and sulfur content engine oils. In order to accomplish this, a large number of proposed lubricating oil compositions must be tested to determine which compositions may be useful.

Additionally, similar changes in specifications and changing customer needs also drive reformulation efforts in other lubricant applications such as, for example, transmission fluids, hydraulic fluids, gear oils, marine cylinder oils, compressor oils, refrigeration lubricants and the like.

However, as stated above, present research in the lubricant industry does not allow for reformulation to occur in an expeditious manner. As such, there exists a need in the art for a more efficient, economical and systematic approach for the preparation of lubricating oil compositions and screening of such compositions for information correlating to the actual useful properties of the compositions. For example, lubricating oils as used in, for example, internal combustion engines of automobiles or trucks, are subjected to a demanding environment during use. The environment results in the oil suffering oxidation which is catalyzed by the presence of impurity species in the oil such as, for example, iron compounds, and is also promoted by the elevated temperatures experienced by the oil during use. The catalyzed oxidation of the oil contributes to the formation of corrosive oxidation products and sludge in the oil but can also cause the viscosity of the oil to increase or even solidify.

Accordingly, it would be desirable to rapidly screen a plurality of sample candidate lubricating oil compositions for oxidation stability utilizing small amounts of each sample. In this manner, a high throughput preparation and screening of a vast number of diverse compositions can be achieved to identify leading lubricating oil compositions.

SUMMARY OF THE INVENTION

A high throughput screening method for determining lubricant performance is provided herein. In accordance with one embodiment of the present invention, a high throughput method for screening lubricating oil compositions, under program control, is provided comprising the steps of (a) providing a plurality of different lubricating oil composition samples comprising (i) a major amount of at least one base oil of lubricating viscosity and (ii) a minor amount of at least one lubricating oil additive, each sample being in a respective one of a plurality of test receptacles; (b) automatically measuring the oxidation stability of each sample to provide oxidation stability data results for each sample; and (c) automatically outputting the results of step (b).

In accordance with a second embodiment of the present invention, a high throughput method for screening lubricating oil compositions, under program control, is provided comprising:

(a) conducting molecular modeling of at least one base oil of lubricating viscosity and at least one lubricating oil additive to provide leading candidates of the at least one base oil of lubricating viscosity and the at least one lubricating oil additive for combination to formulate a leading candidate lubricating oil composition for testing;

(b) containing a plurality of the leading candidate lubricating oil compositions comprising a major amount of at least one leading base oil of lubricating viscosity candidate and a minor amount of at least one leading lubricating oil additive candidate in varying percentages in a plurality of test reservoirs, wherein the major amount of the at least one leading base oil of lubricating viscosity candidate is greater than about 50 wt. %, based on the total weight of the lubricating oil composition;

(c) automatically measuring the oxidation stability of each leading candidate lubricating oil composition to provide oxidation stability data results for each leading candidate lubricating oil composition; and, (d) automatically outputting the results of step (c).

In accordance with a third embodiment of the present invention, a system for screening lubricating oil composition samples, under program control, is provided comprising:

a) a plurality of test receptacles, each containing a different lubricating oil composition sample comprising (i) a major amount of at least one base oil of lubricating viscosity and (ii) a minor amount of at least one lubricating oil additive;

b) a computer controller for automatically selecting individual samples for testing;

c) receptacle moving means responsive to instructions from the computer controller for automatically moving the individually selected samples to a testing station for automatically measuring oxidation stability of the selected samples;

d) means for automatically measuring the oxidation stability of the selected samples to obtain oxidation stability data and for automatically transferring the oxidation stability data to the computer controller.

The methods of the present invention advantageously permits the automatic screening of many different lubricating oil composition samples in an efficient manner in accordance with adjustable selection criteria to determine oxidation stability of the samples.

BRIEF DESCRIPTION OF THE DRAWINGS

Various embodiments are described below with reference to the drawings wherein.

DETAILED DESCRIPTION OF THE PREFERRED EMBODIMENT(S)

Figure 1:
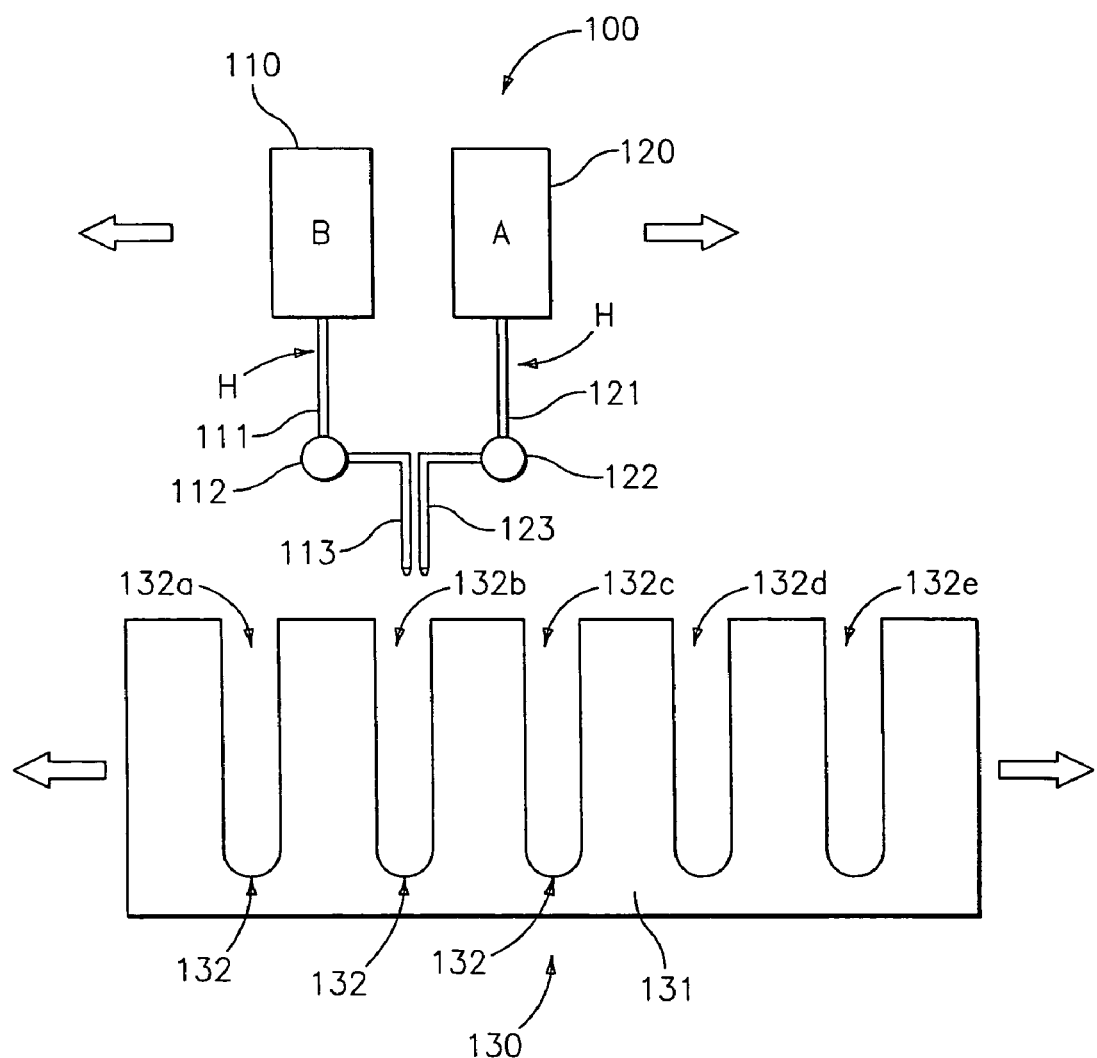
FIG. 1 is a schematic diagram of a system for preparing a plurality of different lubricating oil compositions.

The present invention is directed to a high throughput screening method for determining lubricant performance of a plurality of different lubricating oil compositions by subjecting a plurality of different lubricating oil composition samples in a respective one of a plurality of test receptacles to measure oxidation stability. The expression "high throughput" as used herein shall be understood to mean that a relatively large number of different lubricating oil compositions is rapidly prepared and analyzed. In a first step of the screening method of the present invention, varying quantities of at least one base oil of lubricating viscosity and at least one lubricating oil additive are introduced in respective test reservoirs so that each reservoir contains a different lubricating oil composition having a different composition depending upon the percentage amounts and/or types of the additives combined with the base oil of lubricating viscosity in each receptacle. Data regarding the composition of each sample are stored in a data library. The procedure is advantageously accomplished under program control and is automatically controlled by, for example, a microprocessor or other computer control device. The expression "program control" as used herein shall be understood to mean the equipment used herein in providing the plurality of lubricating oil compositions is automated and controlled by a microprocessor or other computer control device.

The lubricating oil compositions for use in the high throughput screening method of this invention include as a first component a major amount of base oil of lubricating viscosity, e.g., an amount of greater than 50 wt. %, preferably greater than about 70 wt. %, more preferably from about 80 to about 99.5 wt. % and most preferably from about 85 to about 98 wt. %, based on the total weight of the composition. The expression "base oil" as used herein shall be understood to mean a base stock or blend of base stocks which is a lubricant component that is produced by a single manufacturer to the same specifications (independent of feed source or manufacturer's location); that meets the same manufacturer's specification; and that is identified by a unique formula, product identification number, or both. The base oil for use herein can be any presently known or later-discovered base oil of lubricating viscosity used in formulating lubricating oil compositions for any and all such applications, e.g., engine oils, marine cylinder oils, functional fluids such as hydraulic oils, gear oils, transmission fluids, etc. Additionally, the base oils for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 1000 Centigrade (C). Generally, individually the base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fischer-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these preferred base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500-1000, diethyl ether of polypropylene glycol having a molecular weight of 1,000-1,500, etc.) or mono- and polycarboxylic esters thereof such as, for example, the acetic esters, mixed $C_3$-$C_8$ fatty acid esters, or the $C_{13}$ oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The second component of the lubricating oil compositions for use herein is at least one lubricating oil additive. Such additives can be any presently known or later-discovered additive used in formulating lubricating oil compositions. The lubricating oil additives for use herein include, but are not limited to, antioxidants, anti-wear agents, detergents such as metal detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and the like and mixtures thereof. Greases will require the addition of appropriate thickeners. A variety of the additives are known and commercially available. These additives, or their analogous compounds, can be employed for the preparation of the various lubricating oil compositions herein.

Alternatively, the lubricating oil additive(s) can further contain a diluent oil to form an additive concentrate. These concentrates usually include at least from about 90 wt. % to about 10 wt. % and preferably from about 90 wt. % to about 50 wt. %, of a diluent oil and from about 10 wt. % to about 90 wt. %, preferably from about 10 wt. % to about 50 wt. %, of the foregoing additive(s). Suitable diluents for the concentrates include any inert diluent, preferably an oil of lubricating viscosity such as, for example, a base oil as described hereinbelow, so that the concentrate may be readily mixed with lubricating oils to prepare lubricating oil compositions. Suitable lubricating oils that may be used as diluents can be any oil of lubricating viscosity.

Generally the lubricating oil compositions of the present invention will include at least one antioxidant. Examples of antioxidants include, but are not limited to, hindered phenolic antioxidants, secondary aromatic amine antioxidants, sulfurized phenolic antioxidants, oil-soluble copper compounds, phosphorus-containing antioxidants, organic sulfides, disulfides and polysulfides and the like. The antioxidants will ordinarily be present in the lubricating oil compositions of the present invention at a concentration ranging from about 0.1 to about 5 weight percent.

Examples of sterically hindered phenolic antioxidants include, but are not limited to, ortho-alkylated phenolic compounds such as 2,6-di-tertbutylphenol, 4-methyl-2,6-di-tert-butylphenol, 2,4,6-tri-tertbutylphenol, 2-tert-butylphenol, 2,6-diisopropylphenol, 2-methyl-6-tert-butylphenol, 2,4-dimethyl-6-tert-butylphenol, 4-(N,N-dimethylaminomethyl)-2,6-di-tertbutyl phenol, 4-ethyl-2,6-di-tertbutylphenol, 2-methyl-6-styrylphenol, 2,6-distyryl-4-nonylphenol, and their analogs and homologs. Mixtures of two or more such mononuclear phenolic compounds are also suitable.

Examples of other phenol antioxidants for use in the lubricating oil compositions of the present invention include, but are not limited to, methylene-one or more of bridged alkylphenols, one or more sterically-hindered unbridged phenolic compounds and mixtures thereof. Examples of methylene-bridged compounds include, but are not limited to, 4,4'-methylenebis(6-tert-butyl o-cresol), 4,4'-methylenebis(2-tert-amyl-o-cresol), 2,2'-methylenebis(4-methyl-6-tert-butylphenol), 4,4'-methylene-bis(2,6-di-tertbutylphenol), and the like. Particularly preferred are mixtures of methylene-bridged alkylphenols such as those described in U.S. Pat. No. 3,211,652, the contents of which are incorporated by reference herein.

Amine antioxidants can also be used in the lubricating oil compositions of this invention. Examples include, but are not limited to, oil-soluble aromatic secondary amines, aromatic secondary polyamines and the like and combinations thereof with aromatic secondary amines being preferred. Examples of aromatic secondary monoamines include diphenylamine, alkyl diphenylamines containing 1 or 2 alkyl substituents each having up to about 16 carbon atoms, phenyl-alpha-naphthylamine, phenyl-beta-napthylamine, alkyl- or aralkyl-substituted phenyl-alpha-naphthylamine containing at least one or two alkyl or aralkyl groups each having up to about 16 carbon atoms, alkyl- or aralkyl-substituted phenyl-beta-naphthylamine containing at least one or two alkyl or aralkyl groups each having up to about 16 carbon atoms, and the like.

A preferred type of aromatic amine antioxidant is an alkylated diphenylamine of the general formula

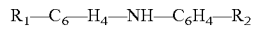

$R_1$—$C_6$—$H_4$—NH—$C_6H_4$—$R_2$ wherein $R_1$ is an alkyl group (preferably a branched alkyl group) having 6 to 12 carbon atoms and preferably 8 or 9 carbon atoms; and $R_2$ is a hydrogen atom or an alkyl group (preferably a branched alkyl group) having 6 to 12 carbon atoms and preferably 8 or 9 carbon atoms. Most preferably, $R_1$ and $R_2$ are the same. One such preferred compound is available commercially as Naugalube 438L, a material which is understood to be predominately a 4,4'-dinonyldiphenylamine (i.e., bis(4-nonylphenyl)(amine) wherein the nonyl groups are branched.

Another antioxidant for use in the lubricating oil compositions of this invention is comprised of one or more liquid, partially sulfurized phenolic compounds such as those prepared by reacting sulfur monochloride with a liquid mixture of phenols wherein at least about 50 weight percent of the mixture of phenols is composed of one or more reactive, hindered phenols and in proportions to provide from about 0.3 to about 0.7 gram atoms of sulfur monochloride per mole of reactive, hindered phenol so as to produce a liquid product. Typical phenol mixtures useful in making such liquid product compositions include a mixture containing by weight about 75% of 2,6-di-tert-butylphenol, about 10% of 2-tert-butylphenol, about 13% of 2,4,6-tri-tertbutylphenol, and about 2% of 2,4-di-tertbutylphenol. The reaction is exothermic and is preferably kept within the range of about 15° C. to about 70° C., most preferably between about 40° C. to about 60° C.

Mixtures of different antioxidants can also be used in the lubricating oil compositions of the present invention. One suitable mixture is comprised of a combination of (i) an oil-soluble mixture of at least three different sterically-hindered tertiary butylated monohydric phenols which is in the liquid state at 25° C., (ii) an oil-soluble mixture of at least three different sterically-hindered tertiary butylated methylene-bridged polyphenols, and (iii) at least one bis(4-alkylphenyl) amine wherein the alkyl group is a branched alkyl group having 8 to 12 carbon atoms, the proportions of (i), (ii) and (iii) on a weight basis falling in the range of about 3.5 to about 5.0 parts of component (i) and about 0.9 to about 1.2 parts of component (ii) per part by weight of component (iii). Examples of such antioxidants discussion above are disclosed in U.S. Pat. No. 5,328,619, the contents of which are incorporated by reference herein. Other useful antioxidants are those disclosed in U.S. Pat. No. 4,031,023, the contents of which are incorporated by reference herein.

Examples of antiwear agents include, but are not limited to, zinc dialkyldithiophosphates and zinc diaryldithiophosphates, e.g., those described in an article by Born et al. entitled "Relationship between Chemical Structure and Effectiveness of Some Metallic Dialkyl- and Diaryl-dithiophosphates in Different Lubricated Mechanisms", appearing in Lubrication Science 4-2 Jan. 1992, see for example pages 97-100; aryl phosphates and phosphites, sulfur-containing esters, phosphosulfur compounds, metal or ash-free dithiocarbamates, xanthates, alkyl sulfides and the like and mixtures thereof.

Examples of detergents include, but are not limited to, overbased or neutral detergents such as sulfonate detergents, e.g., those made from alkyl benzene and fuming sulfuric acid; phenates (high overbased or low overbased), high overbased phenate stearates, phenolates, salicylates, phosphonates, thiophosphonates, ionic surfactants and the like and mixtures thereof. Low overbased metal sulfonates typically have a total base number (TBN) of from about 0 to about 30 and preferably from about 10 to about 25. Low overbased metal sulfonates and neutral metal sulfonates are well known in the art.

Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof.

Examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, preferably a $C_6$ to $C_{24}$, and most preferably a $C_6$ to $C_{20}$, fatty acid ester and a nitrogen-containing compound selected from the group consisting of ammonia, and an alkanolamine, e.g., those disclosed in U.S. Ser. No. 10/402,170, filed Mar. 28, 2003, the contents of which are incorporated by reference herein, and the like and mixtures thereof.

Examples of antifoaming agents include, but are not limited to, polymers of alkyl methacrylate; polymers of dimethylsilicone and the like and mixtures thereof.

Examples of ashless dispersants include, but are not limited to, polyalkylene succinic anhydrides; non-nitrogen containing derivatives of a polyalkylene succinic anhydride; a basic nitrogen compound selected from the group consisting of succinimides, carboxylic acid amides, hydrocarbyl monoamines, hydrocarbyl polyamines, Mannich bases, phosphonoamides, thiophosphonamides and phosphoramides; thiazoles, e.g., 2,5-dimercapto-1,3,4-thiadiazoles, mercaptobenzothiazoles and derivatives thereof; triazoles, e.g., alkyltriazoles and benzotriazoles; copolymers which contain a carboxylate ester with one or more additional polar function, including amine, amide, imine, imide, hydroxyl, carboxyl, and the like, e.g., products prepared by copolymerization of long chain alkyl acrylates or methacrylates with monomers of the above function; and the like and mixtures thereof. The derivatives of these dispersants, e.g., borated dispersants such as borated succinimides, may also be used. Preferably, the dispersants are polyalkylene succinimides derived from animation of polyalkylene succinic anhydrides with polyalkylene polyamine.

If desired, prior to dispensing the at least one base oil and at least one lubricating oil additive to provide the compositions herein, as discussed hereinbelow, it can be advantageous to conduct molecular modeling of proposed compounds for use in the compositions (i.e., formulations) to determine which compounds may provide potential leading candidate compositions. For example, calculations can be carried out involving such factors as, for example, transition states, bond lengths, bond angles, dipole moment, hydrophobicity, etc, of the compounds. Accordingly, the proposed compounds can be screened to determine, for example, which compounds may perform poorly in an oxidation inhibition process due to a poor ability to trap intermediate peroxides. This can be carried out using known software such as, for example, Quantum Mechanics available from Accelrys (San Diego, Calif.).

Software for the design of test libraries can be used to design the original compound test libraries based on input from the foregoing experimental program(s). This software can be used to efficiently design test libraries that cover the desired experimental space and utilize statistical experimental design methods. Other software can then be used to analyze the data from the experiments and correlate that data with the structure of the compounds and/or compound treatment conditions and/or reaction conditions. Such correlations are often referred to as QSAR software (Quantitative Structure Activity Relations) available from Accelrys (San Diego, Calif.). Such QSAR programs can then be used by the software to design subsequent compound test libraries for further screening.

The use of such QSAR programs can add to the efficiency of screening. As more data is collected, these QSAR programs can become more efficient at developing compounds libraries with increased probability for finding desirable compounds. For example, the compounds analyzed can be formulated into various lubricating oil compositions, as described herein, and then further analyzed by way of, for example, regression and analysis technologies, using known software, e.g., $C^2$-QSAR available from Accelrys (San Diego, Calif.). In this manner, validation of the data obtained from the molecular modeling can be achieved and then this data can also be stored in a data collector. In this way, new compounds, conceived by one skilled in the art can be checked by the QSAR software to predict their activity prior to their actual synthesis. Additionally, such software tools may be utilized to prioritize a list of possible compounds being considered for synthesis in such a way that one skilled in the art will have a higher probability for success.

Referring now to FIG. 1, an example of a system to provide the foregoing compositions in the plurality of respective test receptacles is generally illustrated as system 100. Representative of this system and method for providing the foregoing compositions in the plurality of respective test receptacles is one disclosed in U.S. Patent Application Publication No. 20050095714 and entitled "HIGH THROUGHPUT PREPARATION OF LUBRICATING OIL COMPOSITIONS FOR COMBINATORIAL LIBRARIES", the contents of which are incorporated by reference herein. Generally, vessel 110 contains a supply of the foregoing base oils of lubricating viscosity B. Vessel 120 contains a supply of additive A, which can be any of the foregoing additives useful for modifying the properties of the base oil. As one skilled in the art would readily appreciate, one or more of vessels 110 and vessels 120 can be used when dispensing more than one base oil and/or more than one additive, respectively.

Tubular line 111 is a conduit for communicating the base oil B to nozzle portion 113, from which it can be dispensed into a selected test reservoir, as described below. The amount of base oil dispensed is determined by metering pump 112, which can be computer controlled.

Tubular line 121 is a conduit for communicating the lubricating oil additive A to nozzle portion 123, from which it can be dispensed into a selected test reservoir, as described below. The amount of lubricating oil additive dispensed is determined by metering pump 122, which also can be computer controlled. Computer programs and systems for automatically metering predetermined amounts of materials in accordance with a preselected protocol are known in the art and can be used herein.

Nozzles 113 and 123 are preferably in close proximity so that base oil B and additive A can be simultaneously dispensed in a test reservoir. Alternatively, base oil B and additive A can be sequentially added to the test reservoir. The nozzles 113 and 123 can comprise a multichannel pipette or one or more syringe needles.

The vessels 110 and 120 can be under pressure. Optionally, more than two vessels can be employed. Metering pumps suitable for use in the invention are known and commercially available. In the event that highly viscous lubricant base stock or additives are used, the vessels 110 and 120 and/or the tubular lines 111 and 121, metering pumps 112 and 122, and/or nozzles 113 and 123 can be heated to facilitate fluid flow therethrough.

The test frame 130 includes a block 131 of transparent material (e.g., glass) having a plurality of recesses 132 for receiving the dispensed additives or base oil and additives. The recesses provide test reservoirs wherein each reservoir contains lubricating oil compositions of a different and predetermined composition, i.e., the percentage and/or type of base oil and/or additives in each composition will vary from one reservoir to another. Optionally, the reservoirs can be individual receptacles (e.g., test tubes) mounted upon a rack, instead of being recesses in a block. Preferably, the test receptacles comprise transparent glass tubes. While five reservoirs, i.e., recesses 132*a*, 132*b*, 132*c*, 132*d*, 132*e*, are illustrated in FIG. 1, any number of reservoirs can be employed herein. For example the system can employ 20, 50, 100 or even more test receptacles and samples as required.

The individual reservoirs are adapted to hold relatively small amounts of lubricating oil samples. The sample size in each reservoir can generally be no more than about 20 ml, preferably no more than about 15 ml, more preferably no more than about 10 ml and yet more preferably no more than about 5 ml.

The test frame 130 and dispensing nozzles 113 and 123 are movable relative to one another. Although manual movement of the apparatus by an equipment operator is within the purview of the invention, robotic mechanisms with programmable movement are preferred. In one embodiment the test frame 130 is mounted upon a slidable carriage movable in a lateral and/or vertical direction so as to sequentially position a selected recess under the dispensing nozzles 113 and 123. In another embodiment, the nozzles 113 and 123, and optionally the vessels 110 and 120, are slidably movable laterally and/or vertically to accomplish positioning of the nozzles 113 and 123.

In a testing procedure, vessels 110 and 120 are filled with the selected lubricant base oil and additive(s), respectively. The apparatus of system 100 is moved such that dispensing nozzles 113 and 123 are positioned above and in alignment with recess 132*a*. A metered amount of base oil B and a metered amount of additive A are simultaneously dispensed into recess 132*a*. The dispensing nozzles 113 and 123 are thereafter repositioned to be in alignment with the next recess 132*b* and the metered amounts of additive A and/or base oil B are changed in accordance with a predetermined schedule of variation such that the lubricating oil in recess 132*b* has a different percentage composition of additive than that in recess 132*a*. The pattern is repeated as the nozzles 113 and 123 are sequentially aligned with the successive recesses 132*c*, 132*d*, and 132*e* so that each recess has a predetermined composition of lubricating oil.

The components A and B are preferably combined in the reservoirs by mixing, for example, by agitation of the frame 131, static mixing, individual stirring of the contents of the reservoirs (mechanical or magnetic stirring) and/or by bubbling the reservoir with gas, e.g., nitrogen. Optionally, base oil B and additive(s) A can be combined prior to dispensing into the respective reservoirs. For example, a single dispensing nozzle having a mixing chamber can be used, wherein base oil B and additive(s) A are metered into the mixing chamber and then dispensed through the nozzle into the reservoir.

Figure 2:
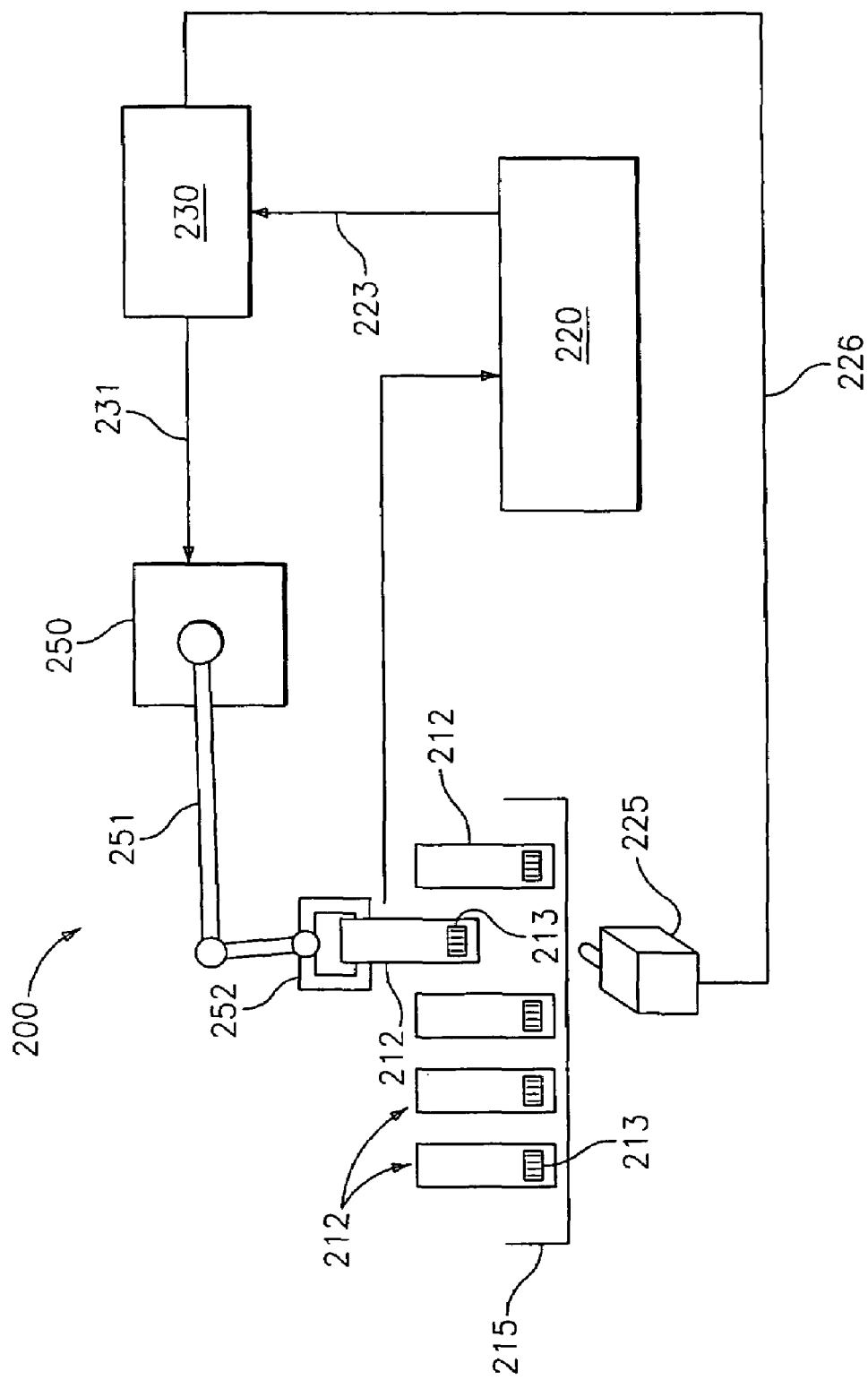
FIG. 2 is a schematic diagram of a system for high throughput oxidation screening of a variety of lubricant oil compositions; and, FIG. 3 is a schematic diagram of a photocell system for measuring deposit formation on a substrate.

Once the plurality of receptacles have been provided containing lubricating oil compositions, the plurality of fluid samples can then be analyzed for oxidation stability measurements such as, e.g., oxidation consumption data, deposit data, viscosity data, etc. Referring now to FIG. 2, a system for sequentially analyzing a plurality of fluid samples for antioxidant properties is schematically illustrated. System 200 is schematically illustrated wherein an array of test receptacles 212 are mounted in a holder 215. The system 200 is adapted to accommodate any number of test receptacles 212 (and samples). Each sample is identifiable, for example, by the position of its test receptacle in an ordered array in holder 215, or more preferably by having an identifying mark associated with it. For example, each test receptacle 212 can include an identifying bar code 213 affixed to the outer surface thereof. A bar code reader 225 is positioned so as to be able to read the individual bar codes of the respective test receptacles 212 and to transmit a bar code data signal to a computer controller 230 via a data transmission line 226 to electronically identify the sample. The bar code reader 225 is preferably movable with respect to the holder 215 in response to a signal from computer controller 230 so as to be positionable in alignment with selected individual test receptacles 212.

A robotic assembly 250 includes a movable arm 251 with a grasping mechanism 252. The robotic assembly is adapted to grasp an individual test receptacle 212 in accordance with selection instructions from computer controller 230 and move the test receptacle to a position in testing station 220 so that the sample in the receptacle can be measured for antioxidant properties. The computer controller 230 is operatively associated with controls to the robotic assembly via control signal transmission line 231 to selectively retrieve predetermined test receptacles for measurement and then replace them in their assigned respective positions in the holder 215.

Testing station 220 includes means for testing the samples for oxidation stability, i.e., resistance to oxidation. Oxidation stability data results of the test are converted to an electrical or optical signal and transmitted via signal transmission line 223 to computer controller 230. Various means for oxidation stability testing are known and generally include subjecting the sample to an oxygen environment and measuring the effect of oxidation upon the sample over a predetermined period of time.

For example, in one test method for use herein (known as the Lube Oil Oxidator test method), a sample of oil is weighed into an oxidator cell, e.g., glass. A glass stirrer is inserted into the cell, and the cell is sealed together with a delivery source of oxygen gas which is maintained at about one atmosphere pressure (760 mmHg). Typically, the stirrer is magnetically coupled to a stir motor which is external to the oxidator cell. To an area above the oil sample can be placed a sufficient solid material suitable for absorption of carbon dioxide gas which may be liberated during oxidation of the test lube oil, e.g., potassium hydroxide. Optionally, a liquid catalyst may be added to the lube oil to assist in accelerating oxidation and is chosen to simulate the types of metal ions typically found in an internal combustion engine.

The cell is then placed in an oil bath maintained at a predetermined temperature, e.g., a temperature ranging from about 250° F. to about 400° F. and preferably from about 300° F. to about 350° F., and connected to an oxygen supply. A sufficient quantity of oxygen is delivered into the cell while the stirrer agitates the oil sample. The test is run until the quantity of oxygen is consumed by the sample and the total time, e.g., in hours, of the sample run is reported. In general, large scale operation typically requires one liter of oxygen for a 25 gram sample. Accordingly, methods employing a smaller quantity of sample require proportionately smaller volumes of oxygen and are within the purview within the purview of one skilled in the art. If desired, results from measurements of the current quantity of oxygen that is consumed as well as the lube oil viscosity can be recorded at predetermined time intervals to a computer database for later analysis. In a variation of this test, the amount of oxygen consumed after a predetermined time period, e.g., about a 10 hour test, is measured while recording to a computer database at time intervals the volume of oxygen uptake and the lube oil viscosity. Suitable high throughput methods for measuring viscosity are disclosed in EP 1158290, WO 99/18431, US 2003/0037601, U.S. Pat. No. 6,383,898, and WO 03/019150.

In a second embodiment, a method to determine the temperature where a test oil undergoes oxidation and deposit formation on, for example, a transparent tube, is used. In this method, the transparent glass tube can be placed inside a metal heating block, e.g., an aluminum heating block, and a small air hose is attached to a holder at the bottom of the glass tube. Next, a suitable nozzle, e.g., about a 5 ml syringe, and a suitable hose, e.g., about a 12 inch flexible tubing, are filled with the oil sample.

The tubing is attached to a holder on the glass tube above the air hose and oil is steadily introduced into the glass tube by the nozzle. Air forces the test oil up the glass tube through the heating block for the duration of the test. The rate of air flow and sample introduction are controlled such that the entire sample is injected within a predetermined time, e.g., a 16 hour time period. The oxidation of the oil gradually forms a dark deposit on the inner wall of the glass tube. The heating block is temperature controlled within small limits and the test conditions are generally chosen over a range of temperatures, e.g., from about 230° C. to about 330° C., and tests can be run at different temperatures to determine deposit formation over a temperature range. After a predetermined period of time (e.g., 16 hours) the glass tube is removed from the test apparatus, rinsed with a suitable solvent, and the amount of deposit is measured in accordance with the darkness of the deposit in the tube, the darkness indicating the quantity of the deposit and the amount of oxidation. The measurement is compared against a predetermined standard set of tubes.

While the determination of the deposit formation can be performed manually by visually inspecting the test tube, comparing it with the standard set of tubes, and estimating the degree of deposit formation, the present method is automated and preferably employs a light source and a photocell. The amount of deposit can be measured by directing a beam of light from the light source through the tube and measuring the amount of light transmitted through the tube by means of the photocell. The opacity of the tube indicates the amount of deposit, and hence, the amount of oxidation of the sample.

Figure 3:
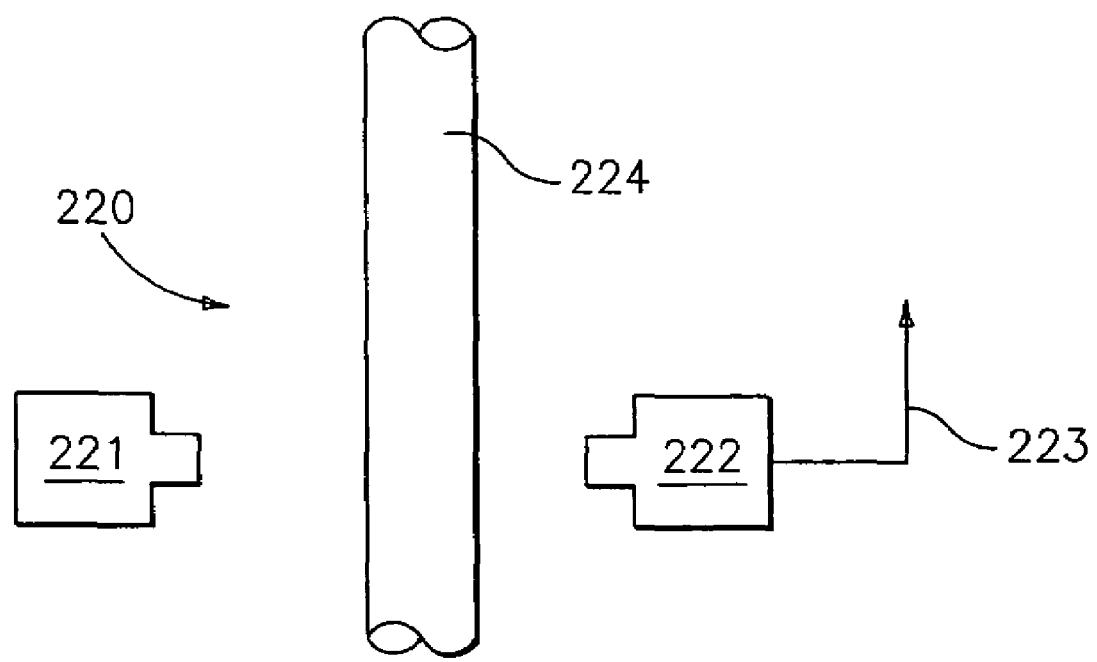

For example, referring to FIG. 3, test tube 224 from the Komatsu Hot Tube testing apparatus is positioned between light source 221 and photocell 222. A beam of light from the light source is directed through the test tube 224 and is measured by the photocell 222, which measures the amount of transmitted light, converts this reading to an electrical signal, and transmits the signal via line 223 to the computer controller 230. The computer controller 230 has stored values of light transmittance (or opacity) for the standard set of tubes and rates the oxidation value of the test sample by comparison with the standard set. The oxidation rating is assigned to the test sample (which can be identified by the bar code) and the information is stored as a component of the data library. The computer controller can thereafter modify the selection instructions. Programming to accomplish the various functions of the computer controller 230 are within the purview of those with skill in the art.

In another oxidation stability test method of the present invention, each of the foregoing samples can be placed in an oxidation container and maintained at a predetermined temperature for a predetermined time. The oxidation container can be a material which is suitable for infrared transmittance, e.g., borosilicate glass. The predetermined temperature can ordinarily range from about 100° C. to about 200° C. and preferably from about 140° C. to about 180° C. The predetermined time may vary up to about 40 hours. Additionally, air is bubbled into the test oil at a constant rate of flow and in the presence of a metallic oxidation catalyst, e.g., a combination of metal ions such as copper, lead and aluminum. The air flow rate can be determined by one skilled in the art (e.g., 13.9 L/hr ∀ 0.5 L/hr has been used for a 200-g sample of test oil). The degree of oxidation is then determined by measuring the infrared absorbance of the carbonyl peak at 1710 cm$^{-1}$ using, e.g., a Fourier transform infrared spectrometer (e.g. a Bruker IFS 48 infrared apparatus). As oxidation takes place, the absorbance peak at 1710 cm$^{-1}$ increases owing to oxidation of the test oil as carbonyl-containing functional groups are produced. A suitable high-throughput method for measuring infrared absorbance is taught in US Patent Application No. 2002/0197731. The data is then recorded in a database.

Another oxidation stability test method of the present invention utilizes differential scanning calorimetry. In general, differential scanning calorimetry is a technique to measure oxidation stability of a test oil sample as it is heated. In this method, the sample is placed in a suitable vessel, e.g., a 10-mL air-tight vial, and held at a predetermined temperature, e.g., from about 120° C. to about 200° C., by using a heating source, e.g., an oven.

Automated data collection occurs throughout the experiment with individual data points representing temperature and heat flow between the sample and reference and each time of measurement being recorded. Accordingly, an objective of this test is to measure the thermal stability of an oil sample at a predetermined temperature in air-tight model systems to determine the exothermic release of heat. The temperature at which the exothermic release of heat is observed is called the oxidation onset temperature and is a measure of the oxidative stability of the oil.

In an alternative embodiment of a oxidation stability test method of the present invention (known as the thin film oxygen uptake test (TFOUT) method, e.g., ASTM D 4742), a sample of oil is weighed into a TFOUT glass dish together with a suitable amount of a fuel fraction sample, liquid metal catalyst, and water sample. The sample is placed in a suitable container, e.g., a steel bomb, and charged with a predetermined amount of oxygen, e.g., from about 30 psi to about 90 psi, at room temperature. The container is then submerged in an oil bath maintained at a predetermined temperature, e.g., 120° C. to about 200° C., and rotated at a predetermined speed, e.g., about 50 rpm to about 140 rpm. A chart recorder can constantly monitors the oxygen pressure and when there is a rapid pressure drop the test is over. The time from the start of the test to the rapid pressure drop is recorded. A time greater than a predetermined value is preferred, and is used as the basis for assigning a pass/fail determination.

If desired, an assigned value of oxidation is programmed into the computer controller for "pass/fail" determination. Assigned pass/fail values can be selected based upon performance requirements for specific lubricant applications and prospective operating environments. If the test sample fails by having an excessively high oxidation value, the test sample can be electronically marked and future testing of lubricant oil formulations having the same composition as the sample can be eliminated from further testing for other performance characteristics. By not retesting failed samples the system can be made to operate more efficiently, energy and time being spent only on samples which prospectively meet the desired product specifications.

If desired the results of the method of the present invention can be monitored from a remote location, i.e., a location which is not in direct or at least in visual contact with the system operating the method of the invention. A remote location can be, for example, a central process control system or room which, as part of the overall system for use herein, monitors and controls the system as well as records the outputs of each of the results of the tests being carried out. In this way, it becomes possible for less interaction with personnel being stationed at the location of the system. Suitable data lines, with which the results of the output, as well as control commands, may be transmitted, are known.

Oxidation stability data regarding the lubricating oil compositions can be stored in a relational database to provide a combinatorial lubricating oil composition library. Alternatively, the system may be electrically connected to a signal data collector comprising a computer microprocessor for system operation and control to collect the data from the various tests over an extended period of time to compile the combinatorial lubricating oil composition library. The database can be used to find optimum combinations for a desired product stream, and can be particularly useful when the desired product stream varies depending on market factors. When the product requirements change, appropriate combinations can be selected to prepare the desired product.

Relational database software can be used to correlate the identity of the lubricating oil compositions and the analytical oxidation stability data obtained therefrom. Numerous commercially available relational database software programs are available, for example, from Oracle, Tripos, MDL, Oxford Molecular ("Chemical Design"), IDBS ("Activity Base"), and other software vendors.

Relational database software is a preferred type of software for managing the data obtained during the methods described herein. However, any software that is able to create a "memory map" of the lubricating oil compositions and correlate that information with the information obtained from the storage stability measurements can be used. This type of software is well known to those of skill in the art.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A high throughput method for screening lubricating oil compositions, under program control, comprising:
   a) conducting molecular modeling of at least one base oil of lubricating viscosity and at least one lubricating oil additive to provide leading candidates of the at least one base oil of lubricating viscosity and the at least one lubricating oil additive for combination to formulate a leading candidate lubricating oil composition for testing;
   b) containing a plurality of the leading candidate lubricating oil compositions comprising a major amount of at least one leading base oil of lubricating viscosity candidate and a minor amount of at least one leading lubricating oil additive candidate in varying percentages in a plurality of test reservoirs, wherein the major amount of the at least one leading base oil of lubricating viscosity candidate is greater than about 50 wt. %, based on the total weight of the lubricating oil composition;
   c) automatically measuring the oxidation stability of each leading candidate lubricating oil composition to provide oxidation stability data results for each leading candidate lubricating oil composition; and,
   d) automatically outputting the results of step (c).

2. The method of claim 1, wherein the base oil is a natural or synthetic oil and the lubricating oil additive is selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

3. The method of claim 1, wherein the step of automatically measuring the oxidation stability of each leading candidate lubricating oil composition comprises exposing the leading candidate lubricating oil composition to oxygen at a predetermined temperature for a predetermined time period and determining the amount of oxygen consumed by the composition.

4. The method of claim 1, wherein the step of automatically measuring the oxidation stability of each leading candidate lubricating oil composition comprises exposing the leading candidate lubricating oil composition to a predetermined amount of oxygen at a predetermined temperature for a predetermined time period and determining the amount of time required for the leading candidate lubricating oil composition to consume the predetermined amount of oxygen.

5. The method of claim 1, wherein the step of automatically measuring the oxidation stability of each leading candidate lubricating oil composition comprises subjecting the leading candidate lubricating oil composition to oxidation reaction conditions in the presence of a substrate and determining the amount of deposit formed on the substrate after a predetermined period of reaction time.

6. The method of claim 1, wherein the step of automatically measuring the oxidation stability of each leading candidate lubricating oil composition comprises using infrared spectroscopy.

7. The method of claim 1, wherein the step of automatically measuring the oxidation stability of each leading candidate lubricating oil composition is determined by differential scanning calorimetry.

8. The method of claim 1, wherein in step (d) the results of step (c) for each leading candidate lubricating oil composition are transmitted to a computer, wherein the computer compares the results with a predetermined value delimiting a failure or passing of the results, and the computer identifies failed leading candidate lubricating oil compositions to preclude further testing of the failed leading candidate lubricating oil compositions.

9. The method of claim 1, wherein the step of automatically outputting comprises converting the oxidation stability data results of step (c) into a digital signal and sending the digital signal to a microprocessor.

10. The method of claim 9, further comprising the steps of compiling the oxidation stability data results sent to the microprocessor in an electronically stored database and constructing therefrom a combinatorial lubricating oil composition library.

11. The method of claim 1, wherein the step of molecular modeling is carried out using a computer molecular modeling program.

12. The method of claim 1, wherein the base oil is a natural or synthetic oil.

13. A system for screening lubricating oil composition samples, under program control, comprising:
   a) means for conducting molecular modeling of at least one base oil of lubricating viscosity and at least one lubricating oil additive to provide leading candidates of the at least one base oil of lubricating viscosity and the at least one lubricating oil additive for combination to formulate a leading candidate lubricating oil composition sample for testing;
   b) means for combining selected quantities of a major amount of the leading candidates of the at least one base oil of lubricating viscosity with selected quantities of a minor amount of the leading candidates of the at least one lubricating oil additive in a plurality of test receptacles to form a plurality of leading candidate lubricating oil composition samples in the plurality of test receptacles;

c) a computer controller for automatically selecting individual samples for testing;

d) receptacle moving means responsive to instructions from the computer controller for automatically moving the individually selected samples to a testing station for automatically measuring oxidation stability of the selected samples; and e) means for automatically measuring the oxidation stability of the selected samples to obtain oxidation stability data and for automatically transferring the oxidation stability data to the computer controller.

14. The system of claim 13, wherein the receptacle moving means comprises a movable carriage.

15. The system of claim 13, wherein the receptacle moving means comprises a robotic assembly having a movable arm for automatically grasping and automatically moving a selected individual receptacle.

16. The system of claim 13, wherein the means for automatically measuring oxidation stability comprises means for automatically measuring the consumption of oxygen of the selected samples.

17. The system of claim 13, wherein the means for automatically measuring oxidation stability comprises means for automatically measuring deposit formation on a transparent glass substrate resulting from oxidation of the selected samples.

18. The system of claim 17, wherein the means for automatically measuring deposit formation includes a light source and a photocell aligned with the light source.

19. The system of claim 13, wherein each test receptacle has a bar code affixed to an outer surface thereof.

* * * * *